United States Patent
McDonnell et al.

(10) Patent No.: US 7,803,315 B2
(45) Date of Patent: Sep. 28, 2010

(54) DECONTAMINATION OF SURFACES CONTAMINATED WITH PRION-INFECTED MATERIAL WITH GASEOUS OXIDIZING AGENTS

(75) Inventors: Gerald E. McDonnell, Chardon, OH (US); Kathleen M. Antloga, Chardon, OH (US); Herbert J. Kaiser, Poontoon Beach, IL (US)

(73) Assignee: American Sterilizer Company, Mentor, OH (US)

(*) Notice: Subject to any disclaimer, the term of this patent is extended or adjusted under 35 U.S.C. 154(b) by 1699 days.

(21) Appl. No.: 10/116,090

(22) Filed: Apr. 3, 2002

(65) Prior Publication Data

US 2003/0086820 A1 May 8, 2003

Related U.S. Application Data

(60) Provisional application No. 60/327,460, filed on Oct. 5, 2001.

(51) Int. Cl.
*A61L 9/00* (2006.01)
*A61L 2/00* (2006.01)
*B08B 9/00* (2006.01)
*B08B 3/00* (2006.01)

(52) U.S. Cl. .............. 422/1; 422/28; 422/32; 422/34; 422/292; 422/300; 422/305; 422/307; 134/22.17; 134/22.19; 134/26

(58) Field of Classification Search .......... 422/1, 422/28, 32, 34, 305, 307, 292, 300; 134/22.17, 134/22.19, 26
See application file for complete search history.

(56) References Cited

U.S. PATENT DOCUMENTS 3,941,696 A * 3/1976 Melnick et al. ............ 210/755

(Continued)

FOREIGN PATENT DOCUMENTS

EP 0 774 263 A1 5/1997

(Continued)

OTHER PUBLICATIONS

XP-002228686, Inactivation of prions in daily medical practice, J.C. Darbord, Biomed&Pharmacother 1999;53:34-8.*

(Continued)

*Primary Examiner*—Jill Warden
*Assistant Examiner*—Monzer R Chorbaji
(74) *Attorney, Agent, or Firm*—Fay Sharpe LLP

(57) ABSTRACT

A surface which carries a material which is infected with prions is cleaned with an alkaline cleaning solution to remove as much proteinaceous material as possible from the surface. The solution contains an alkaline cleaning agent which attacks prions remaining on the surface and which attacks prions removed from the surface during the cleaning step. After the cleaning step, the surface is exposed to a strong gaseous oxidant, preferably hydrogen peroxide vapor. The hydrogen peroxide or other strong oxidant attacks the prions, particularly the unclumped prion strands, deactivating the prions.

22 Claims, 9 Drawing Sheets

U.S. PATENT DOCUMENTS

| | | | | |
|---|---|---|---|---|
| 4,169,123 | A | * | 9/1979 | Moore et al. ................. 422/29 |
| 4,281,674 | A | * | 8/1981 | Tanaka et al. .............. 134/95.2 |
| 4,731,222 | A | * | 3/1988 | Kralovic et al. .............. 422/37 |
| 4,973,449 | A | | 11/1990 | Kolstad et al. |
| 5,007,232 | A | | 4/1991 | Caudill |
| 5,145,642 | A | | 9/1992 | Feathers, III et al. |
| 5,173,259 | A | | 12/1992 | Bordini |
| 5,178,841 | A | | 1/1993 | Vokins et al. |
| 5,258,162 | A | | 11/1993 | Andersson et al. |
| 5,298,222 | A | * | 3/1994 | O'Leary ...................... 422/28 |
| 5,425,815 | A | * | 6/1995 | Parker et al. .................. 134/26 |
| 5,600,142 | A | | 2/1997 | Van Den Berg et al. |
| 5,634,880 | A | | 6/1997 | Feldman et al. |
| 5,674,450 | A | * | 10/1997 | Lin et al. ..................... 422/29 |
| 5,733,503 | A | | 3/1998 | Kowatsch et al. |
| 5,756,678 | A | * | 5/1998 | Shenoy et al. ............... 530/356 |
| 5,779,973 | A | | 7/1998 | Edwards et al. |
| 5,788,925 | A | | 8/1998 | Pai et al. |
| 5,792,435 | A | | 8/1998 | Mueller et al. |
| 5,837,193 | A | | 11/1998 | Childers et al. |
| 5,848,515 | A | | 12/1998 | Catelli et al. |
| 5,871,692 | A | * | 2/1999 | Haire et al. ................... 422/28 |
| 5,872,359 | A | | 2/1999 | Stewart et al. |
| 5,876,664 | A | | 3/1999 | Childers et al. |
| 6,094,523 | A | | 7/2000 | Zelina et al. |
| 6,387,858 | B1 | * | 5/2002 | Shah et al. .................. 510/161 |
| 6,448,062 | B1 | * | 9/2002 | Huth et al. .................. 435/264 |
| 6,558,620 | B1 | * | 5/2003 | Sanford et al. ............... 422/28 |
| 6,613,278 | B1 | * | 9/2003 | Mills et al. ................... 422/33 |
| 6,696,074 | B2 | * | 2/2004 | Dai et al. .................... 424/423 |

FOREIGN PATENT DOCUMENTS

| | | | | |
|---|---|---|---|---|
| FR | | 2759589 A1 | * | 2/1997 |
| FR | | 2759589 | * | 8/1998 |
| FR | | 27595589 | * | 8/1998 |
| JP | | 04-312440 | | 11/1992 |
| JP | | 08-308912 | | 11/1996 |
| JP | | 11-299867 | | 11/1999 |
| JP | | 2000-245816 | | 9/2000 |
| WO | | WO 94/22305 | * | 10/1994 |
| WO | | WO 98/15297 | | 4/1998 |
| WO | | WO 01/54736 A2 | | 8/2001 |

OTHER PUBLICATIONS

Internet print-out for the publication date of the Disinfection, Sterilization, and Preservation textbook by Seymour S. Block. 5th Edition.*

Disinfection, Sterilization, and Preservation textbook by Seymour S. Block. 4th Edition. pp. 436-439.*

Prione Disease and Medical Devices, ASAIO Journal 2000. pp. S69-S72.*

Disinfection, Sterilization, and Preservation textbook by Seymour S. Block. 5th Edition. pp. 659-674.*

Creutzfeldt-Jakob Disease: Recommendations for Disinfection and Sterilization by William A. Rutala and David J. Weber. HealthCare Epidemiology, CID 2001:32 (May 1). XP 008012867, pp. 1348-1356.*

Prion Disease and Medical Devices by Kathy Antloga et al., ASAIO Journal 2000. XP-001092854.*

Internet printout for the definition of Triton X-100.*

Antloga, et al. "Prion Disease and Medical Devices", ASAIO Journal, V., N. 6, 2000; pp. S69-S72 XP001092854.

Darbord, "Inactivation of Prions in Daily Medical Practice", Biomedicine & Pharmacotherapy, V. 54, 1999 pp. 34-38 XP002228686.

Rutala, et al., "Creutzfeld-Jakob Disease:Recommendations for Disinfection and Sterilization", Clinical Infectious Diseases, V. 32, N. 9, May 2001 pp. 1348-1356 XP008012867.

Samson, "Stérilisation du Matériel de Dermato-Chirurgie au Cabinet du Dermatologue", Nouvelle Dermatologiques, V. 19, N. 1, 2000 pp. 57-60 XP008012868.

* cited by examiner

US 7,803,315 B2

DECONTAMINATION OF SURFACES CONTAMINATED WITH PRION-INFECTED MATERIAL WITH GASEOUS OXIDIZING AGENTS

This application claims the priority of U.S. Provisional Application Ser. No. 60/327,460, filed Oct. 5, 2001.

BACKGROUND OF THE INVENTION

The present invention relates to the field of biological decontamination. The invention finds particular application in connection with the removal and/or destruction of harmful biological materials, such as prions (proteinaceous-infectious agents), from medical, dental, and pharmaceutical instruments and will be described with particular reference thereto. It will be appreciated, however, that the method and system of the present invention may be utilized in biological decontamination of a wide range of equipment, instruments, and other surfaces contaminated with prion infected material, such as pharmaceutical preparation facilities, food processing facilities, laboratory animal research facilities including floors, work surfaces, equipment, cages, fermentation tanks, fluid lines, and the like.

The term "Prion" is used to describe proteinaceous-infectious agents that cause relatively similar brain diseases in humans and/or in animals, which are invariably fatal. These diseases are generally referred to as transmissible spongiform encephalopathies (TSEs). TSEs include Creutzfeldt-Jakob disease (CJD) and variant CJD (vCJD) in humans, Bovine Spongiform Encephalopathy (BSE) in cattle, also know as "Mad Cow Disease," Scrapie in sheep, and Wasting Disease in elk. All of these diseases attack the neurological organs of the animal or animals which are susceptible to the particular disease. They are characterized by initially long incubation times followed by a short period of neurological symptoms, including dementia and loss of coordination, and eventually death.

The infectious agent responsible for these diseases is thought to be a simple protein, with no associated nucleic acids. The pathogenic mechanism for such prion diseases is proposed to involve an initially normal host encoded protein. The protein undergoes a conformational change to an abnormal form (a prion), which has the ability of self-propagation. The exact cause of this change is, at present, unknown. The abnormal form of the protein is not broken down effectively in the body and its accumulation in certain tissues (in particular neural tissue) eventually causes tissue damage, such as cell death. Once significant neural tissue damage has occurred, the clinical signs are observed.

Prion diseases may thus be classified as protein aggregation diseases, which also include several other fatal diseases, such as Alzheimer's disease and amyloidosis. In the case of CJD, the most prevalent prion disease in humans (occurring in roughly 1:1,000,000 of the population), about 85% of cases are thought to arise sporadically, about 10% are thought to be inherited, and about 5% arise iatrogenically.

Although not considered to be highly contagious, prion diseases can be transmitted by certain high risk tissues, including the brain, spinal cord, cerebral spinal fluids, and the eye. After a surgical procedure on a prion infected patient, prion containing residue may remain on the surgical instruments, particularly neurosurgical and ophthalmological instruments. During the long incubation period, it is extremely difficult to determine whether a surgical candidate is a prion carrier.

Different levels of microbial decontamination are recognized in the art. For example, sanitizing connotes free from dirt or germs by cleaning. Disinfecting calls for cleansing in order to destroy harmful microorganisms. Sterilization, the highest level of biological contamination control, connotes the destruction of all living microorganisms.

It is now known that certain biological materials which do not live or reproduce in the conventional sense, such as prions, are nevertheless capable of replication and/or transformation into harmful entities. We use herein the term "deactivation" to encompass the destruction of such harmful biological materials, such as prions, and/or their ability to replicate or undergo conformational changes to harmful species.

Vapor phase sterilization is a known technique for decontaminating or sterilizing the outer surfaces of reusable medical instruments and has been adapted to interstitial sterilization through the selective application of below atmospheric pressures. During vapor phase sterilization, medical instruments are placed in an enclosed space or chamber where sterilization occurs. The items to be sterilized are subjected to either a "deep vacuum" approach or a "flow through" approach. A liquid sterilant is vaporized in a heated vaporizer. Once vaporized, a deep vacuum is used to pull the sterilant vapor into the evacuated and sealed chamber. In the flow through approach, vaporized sterilant is mixed with a flow of carrier gas that delivers the sterilant vapor into, through and out of the chamber. The chamber may be at slightly negative or positive pressure.

For example, Edwards, et al., U.S. Pat. No. 5,779,973 discloses vapor hydrogen peroxide sterilization of plastic-overwrapped IV bags. An open flow-through system is disclosed in Childers, U.S. Pat. No. 5,173,258.

Prions, however, are notoriously very hardy and demonstrate resistance to routine methods of decontamination and sterilization. Unlike microorganisms, prions have no DNA or RNA to destroy or disrupt. Prions, due to their hydrophobic nature, tend to aggregate together in insoluble clumps. Under many conditions that lead to successful sterilization in microorganisms, prions form tighter clumps which protect themselves and underlying prions from the sterilization process. The World Health Organization (1997) protocol for prion deactivation calls for soaking the instrument in concentrated sodium hydroxide or hypochlorite for two hours followed by one hour in an autoclave. These aggressive treatments are often incompatible with medical devices, particularly flexible endoscopes and other devices with plastic, brass, or aluminum parts. Many devices are damaged by exposure to high temperatures. Chemical treatments, such as strong alkali, are damaging to medical device materials or surfaces in general. Glutaraldehyde, formaldehyde, ethylene oxide, liquid hydrogen peroxide, most phenolics, alcohols, and processes such as dry heat, boiling, freezing, UV, ionizing, and microwave radiation have generally been reported to be ineffective. There is a clear need for products and processes that are effective against prions yet compatible with surfaces.

The present invention provides a new and improved method of treatment of surfaces contaminated with prion-infected material which overcomes the above-referenced problems and others.

SUMMARY OF THE INVENTION

In accordance with one aspect of the present invention, a method of deactivating prions is provided. The method includes pretreating surfaces that carry prion infected material with a cleaner that attacks prions and treating the surfaces with an oxidizing agent in gaseous form.

In accordance with another aspect of the present invention, a method of cleaning and decontaminating a surface which has been contaminated with a biological material that includes prions is provided. The method includes cleaning the surface with an alkaline cleaner which has a pH of at least 10 and exposing the cleaned surface to a vapor which includes hydrogen peroxide for a sufficient time to destroy viable prions on the surface.

In accordance with another aspect of the present invention, a prion deactivation system for removing and deactivating prions on an item is provided. The system includes a chamber for receiving the item. A well is fluidly connected with the chamber for receiving a concentrated alkaline cleaner. A supply of water is fluidly connected with the well for providing water to mix with the concentrated alkaline cleaner and form an alkaline cleaning solution. A source of hydrogen peroxide vapor is fluidly connected with the chamber.

In accordance with another aspect of the present invention, a method of treating a surface which is contaminated with prions and biological material is provided. The method includes cleaning the surface to remove the biological material with a cleaner and, after the step of cleaning, decontaminating the surface with a gaseous oxidizing agent at a temperature of from 45-60° C.

One advantage of the present invention is that it is gentle on instruments.

Another advantage of the present invention is that it deactivates prions quickly and effectively.

Another advantage of the present invention is that it is compatible with a wide variety of materials and devices.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
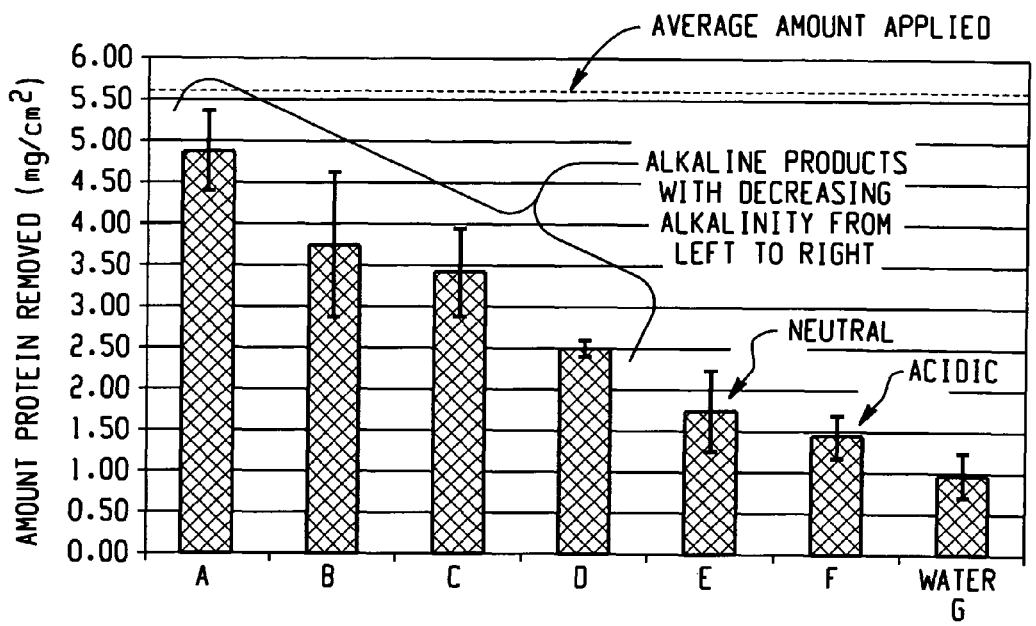
FIG. 1 illustrates proteinaceous material removal with various cleaning compositions.

A method for microbial decontamination and prion deactivation of instruments or other items which carry material which may be contaminated with prions includes a cleaning operation using an alkaline cleaner, followed by treatment with a gaseous or vapor phase oxidizing agent.

The cleaner composition is preferably formed by dilution of a concentrate which includes an alkaline cleaning agent, and optionally includes one or more of the following: a surfactant, a chelating agent, an anti-redeposition agent, a cationic polymer, and a metal corrosion inhibitor. Alternatively, the components of the cleaning composition are separately mixed with water or other suitable solvent.

The alkaline cleaning agent is preferably a hydroxide of an alkali metal or an earth alkali metal. Exemplary alkaline cleaning agents are potassium hydroxide and sodium hydroxide. The hydroxide is preferably present at from 20-60% by weight of the concentrate.

The chelating agent is provided for chelating with water hardness salts, such as salts of calcium and magnesium, which become deposited on the equipment to be cleaned. Suitable chelating agents include, but are not limited to, carboxylic acid-based polymers, such as polyacrylic acid, and ethylenediaminetetraacetic acid (EDTA) or salts thereof. Sodium hexametaphosphate, discussed below, also acts as a chelating agent to some extent. The chelating agent is preferably present from about 1-15% by weight of the concentrate. A preferred concentrate composition includes 2-10% by weight of Na-EDTA and 0.1-3% by weight of polyacrylic acid.

The surfactant is selected from the group consisting of anionic, cationic, nonionic, and zwitterionic surfactants to enhance cleaning performance. Examples of such surfactants include but are not limited to water-soluble salts or higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine.

Additional examples are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Suitable amphoteric surfactants are alkyl amphocarboxylates, such as mixed C-8 amphocarboxylate surfactants. A preferred concentrate includes mixed C8 amphocarboxylates at a concentration of about 0-5% by weight.

The anti-redeposition agent inhibits redeposition of soil on the equipment. Suitable anti-redeposition agents include gluconates, such as sodium gluconate, and citrate salts. Polyacrylic acid also acts as an anti-redeposition agent. The anti-redeposition agent is preferably at a concentration of 1-10% by weight of the concentrate composition. A particularly preferred composition includes polyacrylic acid at a concentration of 0.1-3% by weight, more preferably about 0.3% by weight, and sodium gluconate at a concentration of 1-10% by weight, more preferably about 1-5% by weight of the composition.

The cationic polymer aids in maintaining magnesium, silicate, and zinc compounds in solution, maintains corrosion inhibitors in solution, and aids in preventing water-hardness precipitation and scaling on the cleaning equipment surfaces when the cleaning composition is used in hard water. Exemplary of such cationic polymers are carboxylated polymers which may be generically categorized as water-soluble carboxylic acid polymers, such as polyacrylic or polymethacrylic acids or vinyl addition polymers. Of the vinyl addition polymers contemplated, maleic anhydride copolymers as with vinyl acetate, styrene, ethylene, isobutylene, acrylic acid and vinyl ethers are examples.

Exemplary cationic polymers are dialkyldiallyl ammonium salt (e.g., halide) homopolymers or copolymers, such dimethyldiallyl ammonium chloride homopolymer, dimethyldiallyl ammonium chloride/acrylamide copolymer, dimethyldiallyl ammonium chloride/acrylic acid copolymer, and vinyl imidazolevinyl pyrrolidone copolymers. Other suitable non-cellulosic cationic polymers are disclosed in the CTFA Cosmetic Ingredient Dictionary under the designation "Polyquaternium" followed by a whole number. All of the above-described polymers are water-soluble or at least colloidally dispersible in water. Such low molecular weight carboxylated polymers, molecular weight range from about 1,000 to less than 100,000, act as antinucleating agents to prevent carbonate from forming undesirable scaling in wash tanks. Polyquaternium 7, a dimethyldiallyl ammonium chloride/acrylamide copolymer, is exemplary. The cationic polymer is preferably present at 0-10% by weight of the concentrate.

Exemplary metal corrosion inhibitors are silicic acid salts and phosphoric acid salts in an amount of about 0-10% weight % of the concentrate.

Concentration ranges of a preferred alkali cleaner concentrate are shown in TABLE 1.

TABLE 1

| Ingredient | Recommended Range, wt. % in concentrate |
|---|---|
| 45% Potassium hydroxide | 45-90 |
| 40% Ethylenediamine tetraacetic acid (EDTA), tetrasodium salt | 1-20 |
| Sodium gluconate | 0-7 |
| 30% 2-Propenoic acid homopolymer (Polyacrylic acid) | 1-20 |
| Mixed C8 amphocarboxylates | 0-5 |
| Sodium hexametaphosphate | 0-10 |
| 40% silicic acid, sodium salt | 0-10 |
| 48% acrylic acid homopolymer | 1-20 |
| Dimethyldiallyl ammonium chloride and acrylamide copolymer (Polyquaternium 7) | 0-10 |

In particular, the following formulations are specified in TABLE 2.

TABLE 2

| Component | Formulation A wt % in Cleaner Concentrate | Formulation B wt % in Cleaner Concentrate |
|---|---|---|
| 45% Potassium hydroxide | 69 | 46 |
| 40% Ethylene diamine tetraacetic acid, tetrasodium salt | 20 | 10 |
| Sodium gluconate | 1 | 5 |
| 30% 2-Propenoic acid homopolymer (Polyacrylic acid) | 3 | 1 |
| Mixed C8 amphocarboxylates | 0 | 2 |
| Sodium hexametaphosphate | 0 | 10 |
| Softened water | 7 | 26 |

Note that in TABLES 1 and 2, many of the ingredients are already partially diluted. Thus, for example, the actual concentration of potassium hydroxide in Formulation A of the concentrate is actually about 30% by weight and in Formulation B, about 21% by weight.

To perform the cleaning operation, the cleaning concentrate is diluted in water at about 8-16 cc/liter and the items to be cleaned treated with the cleaning solution, preferably combined with agitation, at 30 to 65° C. for 2-30 minutes. A typical overall cycle in an automatic washer may include a two minute pre-wash with water at 30-65° C., a 2-30 minute wash with the alkaline cleaner at 8-16 cc/liter, a 15 second rinse in water, a one minute thermal rinse at 30-65° C., and finally a drying step (if required). An alternative cycle may simply involve prerinsing, alkaline cleaning, and post-rinsing as described above.

The cleaning concentrate optionally includes a low level of an antimicrobial agent, such as a phenol, quaternary ammonium compound, oxidizing agent, e.g., sodium hypochlorite, hydrogen peroxide, or peracetic acid, or combination thereof.

Other cleaners are also contemplated. Cleaners fall into various categories. Enzymatic cleaners include active proteases, lipases, and other enzymes to aid in tissue or soil breakdown on a surface. These products assist in removing prion and other proteinaceous materials, but generally lack efficacy against prions, i.e., prions are protease resistant. Non-enzymatic cleaners may be broken down into neutral, acidic, and alkali based products. These cleaners include a variety of excipients that aid in soil removal from a surface such as wetting agents and surfactants.

Figure 2:
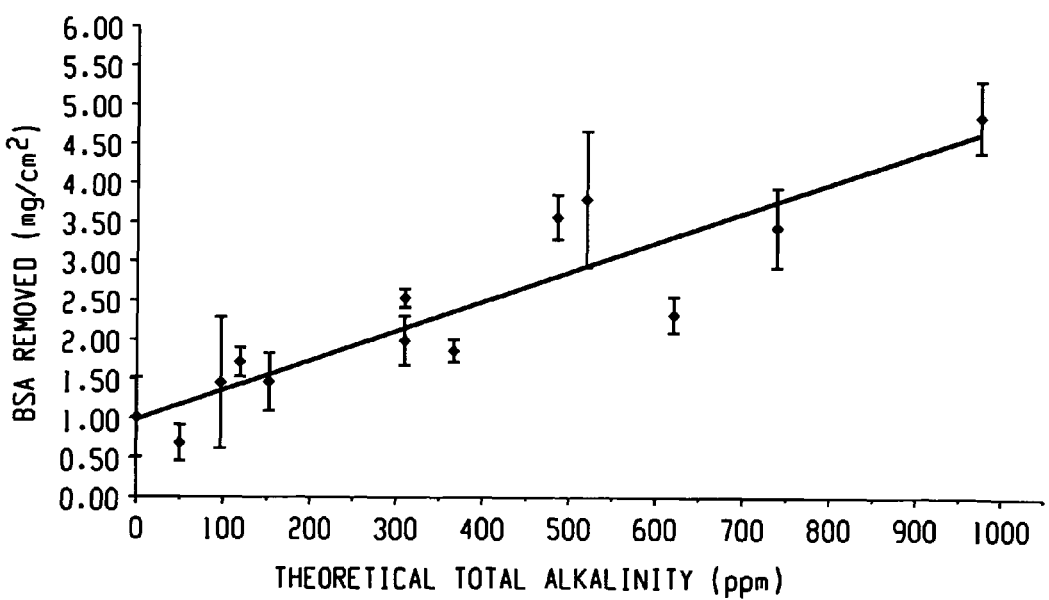
FIG. 2 graphs proteinaceous material versus alkalinity.

Cleaning agents with a range of pHs were tested against a prion model for prion removal efficacy. Bovine serum albumin (BSA), like prions, is proteinaceous in nature and has been shown to exhibit responses to treatment processes which correlate with the response of prions under similar treatments. More specifically, a 5% BSA solution was prepared and 2 ml pipetted onto each of like stainless steel coupons. These coupons were dried at 43° C. in an oven for one hour, cooled to room temperature, and weighed. Under these drying conditions, bovine serum albumin adopts a high β-sheet conformation which is similar to infectious prion protein. The coupons were washed in a STERIS 444™ washer/disinfector using its instrument cycle, but with different cleaning compositions. The instrument cycle includes a 2 minute prewash, a 2 minute wash at 65° C., a rinse, a thermal rinse, and a drying cycle. Following the cycle, the coupons were removed from the washer, cooled, and weighed. FIG. 1 shows the amount of material removed in the washing cycle where compositions A, B, C, and D are alkaline cleaners with decreasing alkalinity from A-D, composition E is a neutral cleaner (Renu-Kenz™, obtainable from STERIS Corp., Mentor Ohio), composition F is an acid cleaner (CIP-220™, obtainable from STERIS Corp.), and composition G is a plain water control. FIG. 2 is a graph of the material removed versus theoretical total alkalinity in parts per million. As shown in FIG. 2, there is a strong correlation between the amount of material removed and the alkalinity, the amount increasing with the total alkalinity of the cleaning composition.

The cleaning composition used as described removes fixed proteinaceous matter including clumps of protein. Any remaining proteinaceous substances are in the form of a thin film which is more easily penetrated by the deactivating agent in a subsequent deactivation step. Moreover, the preferred alkaline cleaner results in about a 50% destruction of prions in the residual film that is not removed during the cleaning step.

Optimized alkaline cleaning formulations based on TABLE 1 were developed and analyzed as described above with the following results:

TABLE 3

| Formulation | Average Protein Removed (mg/cm$^2$) | Standard Deviation | Equivalent [KOH], M, in washer |
|---|---|---|---|
| Water Control | 0.5 | 0.04 | 0 |
| Alkaline 1 | 2.36 | 0.57 | 0.020 |
| Alkaline 2 (A) | 4.18 | 0.52 | 0.033 |
| Alkaline 3 | 2.97 | 0.75 | 0.031 |
| Alkaline 4 | 2.52 | 0.29 | 0.029 |
| Alkaline 5 | 3.56 | 0.18 | 0.035 |
| Alkaline 6 | 2.44 | 0.49 | 0.020 |
| Alkaline 7 | 2.32 | 0.30 | 0.020 |
| Alkaline 8 | 3.11 | 0.17 | 0.033 |
| Alkaline 9 | 2.85 | 0.74 | 0.034 |
| Alkaline 10 | 3.46 | 0.55 | 0.034 |
| Alkaline 11 | 3.53 | 0.52 | Not determined |
| Alkaline 12 (B) | 4.06 | 0.40 | Not determined |
| Alkaline 13 | 3.34 | 0.42 | Not determined |
| Alkaline 14 | 3.49 | 0.20 | Not determined |
| Alkaline 15 | 3.28 | 0.75 | Not determined |

The compositions of the most effective formulations (labeled A and B) are specified above in TABLE 2. Preferred cleaners have an alkalinity equivalent to 0.030 M KOH, or above and a pH of at least 10, preferably, pH 13, or higher.

Figure 3:
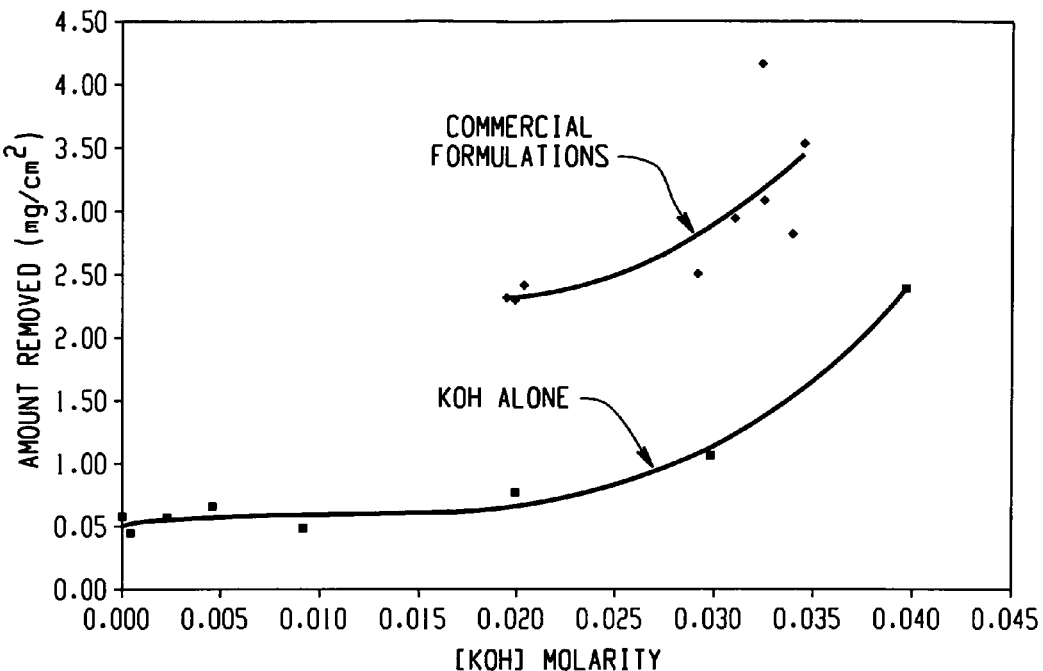
FIG. 3 compares the effect of KOH concentration alone and overall alkalinity in the cleaning formulations in proteinaceous material removal.

The protein removal efficacy is not only a function of alkalinity in these optimized formulations, but on the other components of the composition. This is shown in FIG. 3. The formulations are primarily composed of three component parts: alkalinity ingredients, water control ingredients, and surfactants. The alkalinity ingredients also may act as water control agents. For example, EDTA contributes both alkalinity and water control characteristics to the formulations. Water control agents are preferably included because the quality of the water used to clean surfaces varies considerably and can otherwise affect the efficacy of a given formulation. An example is water hardness, which displays inverse solubility, the higher the temperature the less soluble the water hardness salts are. Water hardness salts are also less soluble at higher pH values. Therefore, the EDTA or other chelating agents are preferably employed to keep the hardness salts in solution. All three of the above component parts are believed to function synergistically to enable the formulation to clean surfaces. This is demonstrated in FIG. 3 which compares the alkalinity equivalents of nine commercial formulations (top curve) to that of KOH (bottom curve) alone as the alkalinity source.

The effect of alkalinity alone was evaluated by adding the respective proportion of potassium hydroxide (KOH) to the washer and testing as described above. Although the effect of alkalinity (expressed as the molarity of KOH) was significant (as demonstrated in the bottom curve of FIG. 3), the formulations tested (examples 1 to 9 from TABLE 3) demonstrated enhanced efficiency of protein removal, e.g. at 0.02 M, the commercial formulations removed 2-2.5 mg/cm$^2$ protein whereas KOH alone removed less than 1 mg/cm$^2$ of protein.

The present inventors have found that proper selection of the cleaning composition not only removes prions and other proteinaceous materials, but also at least partially deactivates the prions. Particularly, alkaline cleaners are more effective in deactivating prions than enzymatic, neutral, or acid cleaners.

Figure 4:
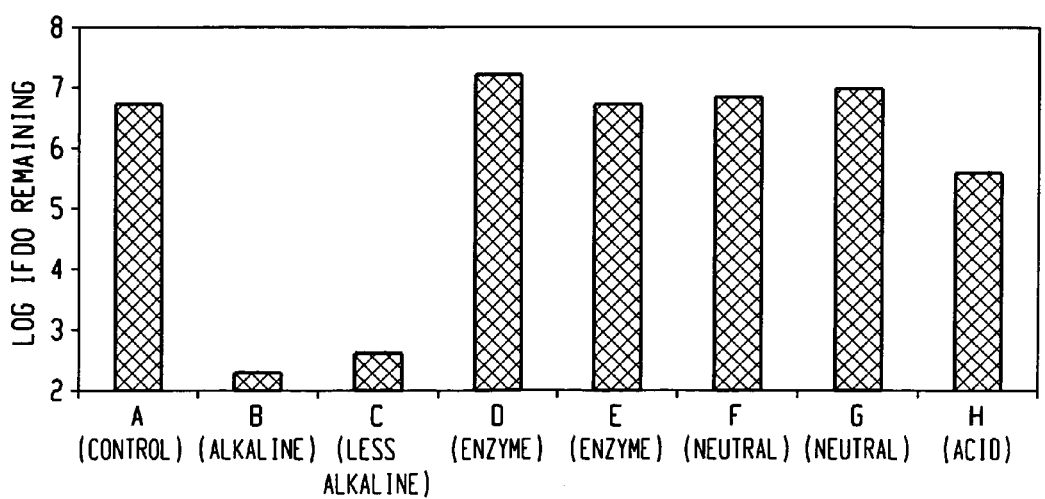
FIG. 4 compares the efficacy of various cleaning compositions in the reduction of a prion (IFDO) model.

A variety of cleaners were tested against a prion model in which an ileal fluid dependent organism (IFDO) was artificially cultured in modified Mycoplasma based broth, quantified by serial dilutions, and plated on a similar agar. The IFDO was originally extracted from ileal fluid hence the name. It has since been found in other parts of the body. The IFDO has shown a strong correlation with actual prions in its response to treatment processes and thus is proposed as a model for prion activity. The formulations were prepared in water and an aliquot of IFDO suspended directly into each. The test solutions were incubated at 40° C. for 30 minutes, aliquot sampled and quantified by serial dilution and plating into a modified growth agar. Following incubation at 37° C. for 48 hours, the plates were counted and log reductions in the IFDO present obtained. These test results are illustrated in FIG. 4, where cleaner A is a control of plain water, cleaner B is an alkaline cleaner (CIP150™), cleaner C is a second, slightly less alkaline cleaner (CIP100™), cleaners D (Klenzyme™) and E (Enzycare 2™) are enzyme cleaners, cleaners F (Renu-Klenz™) and G (NpH-Klenz™) are neutral cleaners, and cleaner H (CIP 220™) is an acid cleaner (each of the tested cleaners was obtained from STERIS Corp.).

Thus, alkali cleaners are not only more effective in removing prion material, they are also significantly more effective in deactivating what prion material might remain, as well as removed prion material still in solution.

After the cleaning step, the instruments or other items are subject to a prion deactivation step. During the prion deactivation step, the items are contacted with a gaseous, plasma, or vapor phase oxidizing agent, all of which will be referred to herein as gaseous oxidizing agents. Preferred gaseous oxidizing agents include hydrogen peroxide vapor, plasma/hydrogen peroxide or peracetic acid, plasma and/or vapor phase peracid, such as peracetic acid vapor, chlorine dioxide gas, and combinations of hydrogen peroxide with one or more peracids. In one embodiment, vapor, such as hydrogen peroxide vapor, is allowed to condense on items to be decontaminated. In a subsequent aeration or evacuation step, the condensed sterilant is reconverted to vapor and is removed from the items. A particularly preferred gaseous oxidant includes hydrogen peroxide vapor. While the system will be described with particular reference to vapor hydrogen peroxide as the prion deactivation agent, it will be appreciated that other gaseous oxidizing agents are also contemplated.

The items to be treated with the gaseous oxidant (which have already been cleaned with alkaline cleaning composition, rinsed, and preferably dried) are positioned in a sterilizing chamber or simply shrouded under a tent, a hood, or other covering. Preferably, the vapor phase prion decontamination takes place at above ambient temperatures, more preferably, from about 25-60° C., most preferably, at about 45-55° C. It is also contemplated that the sterilization could occur in ambient conditions (15-30° C.) provided there is a sufficient flow of sterilant vapor.

In one embodiment, hydrogen peroxide vapor is introduced to a chamber capable of being evacuated. The chamber containing the items to be treated is first evacuated to a pressure of about 100 Torr ($1.33 \times 10^4$ Pa) or below, most preferably, about 10 Torr ($1.33 \times 10^3$ Pa) or less. If the item is not dry when placed in the chamber, the vacuum is held for a period sufficient to evaporate any liquid residue. Hydrogen peroxide vapor is then introduced to the chamber to contact the items. Applying a vacuum prior to introduction of hydrogen peroxide and/or between hydrogen peroxide pulses is believed to aid penetration of the vapor through packaging and into less accessible regions of the item, such as narrow lumens. The hydrogen peroxide concentration is preferably maintained at below its saturation level to avoid condensation on the items and chamber walls, etc. For example, the hydrogen peroxide is maintained at 75-95% saturation. Where the chamber is capable of accurately maintaining % saturation to within 1-5%, the saturation is preferably close to 95%, and may even be higher if the % saturation can be maintained within even closer tolerances.

Figure 5A:
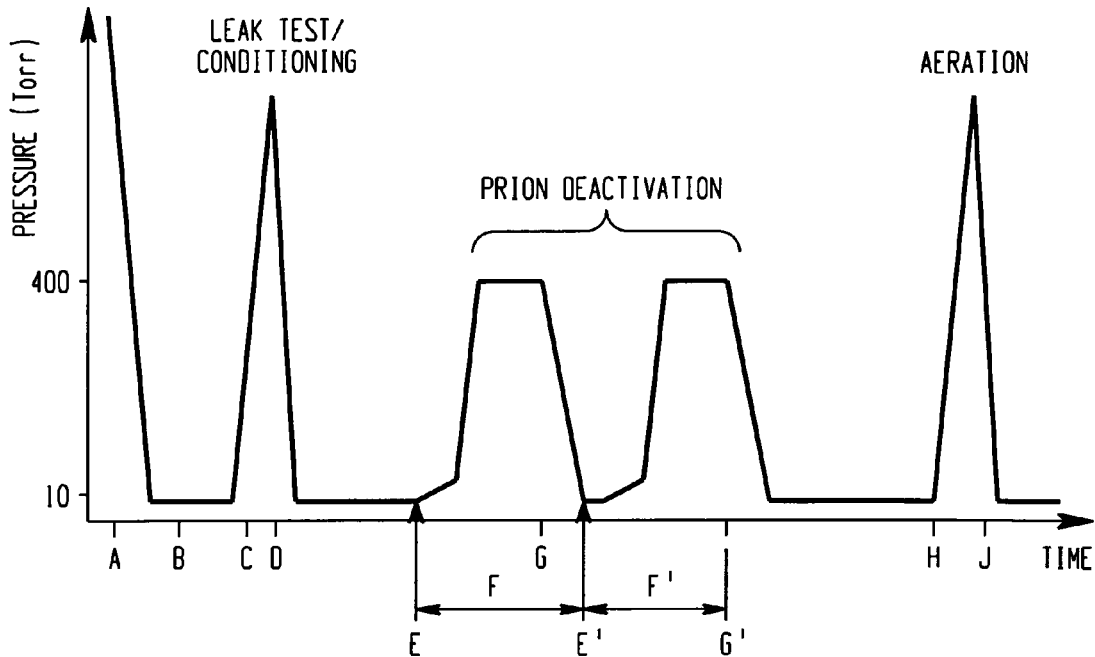
FIG. 5a is a plot showing pressure changes in an exemplary vacuum prion deactivation cycle.
Figure 5B:
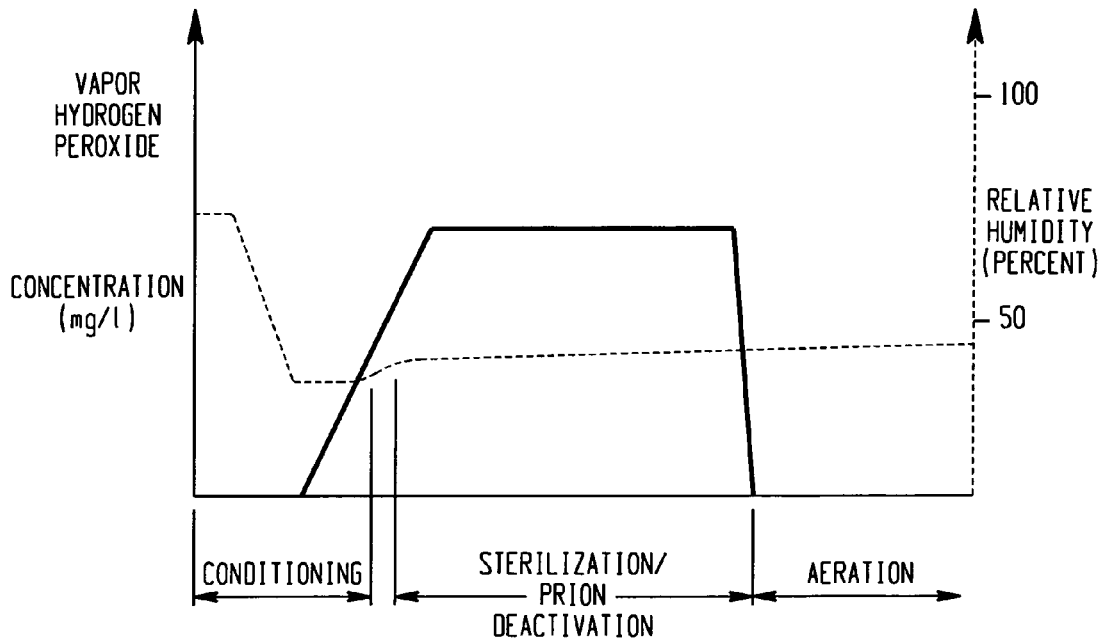
FIG. 5b is a plot showing an exemplary atmospheric cycle.

In a preferred embodiment, two or more pulses of hydrogen peroxide are introduced to the chamber, each one preceded and followed by an evacuation step, as exemplified in FIG. 5. A first step is shown in FIG. 5 as a leak test/conditioning step. This step is carried out in the absence of hydrogen peroxide and includes an evacuation step A (to about 10 Torr, or less), followed by a hold step B, where the pressure inside the chamber is monitored for leaks by observing pressure changes, if any. During step C, dry air is introduced to the chamber to reduce the moisture in the chamber prior to introduction of hydrogen peroxide vapor. The chamber is evacuated once more at D to 10 Torr or less, prior to introduction of hydrogen peroxide at E raising the pressure to about 300-500 Torr. Optionally, a dry gas is introduced to increase the pressure to 500-750 Torr. The hydrogen peroxide contacts the instruments in the chamber for a period of several seconds to several minutes F, then is evacuated at G to a pressure of less than about 10 Torr. Steps E, F, and G are repeated one or more times, shown as E', F', and G'. In a final aeration step, filtered air is introduced to the chamber at H and then evacuated at J to draw with it any remaining hydrogen peroxide which has adsorbed onto the items undergoing prion deactivation. Filtered air is again allowed into the chamber to bring the pressure up to atmospheric before opening the chamber.

Alternatively, prion decontamination with hydrogen peroxide takes place under atmospheric or above atmospheric conditions. When atmospheric or above atmospheric pressures are used, an exemplary prion decontamination cycle includes four phases: dehumidification, conditioning, prion deactivation, and aeration. During dehumidification, the relative humidity is reduced, by drying the atmosphere in the chamber, to below 40% RH, e.g. to about 10-30% RH, for example, by circulating dry air through the chamber. Dry air may be provided by passing air through a desiccant cartridge or using a refrigerated system to extract the moisture. During the conditioning step, hydrogen peroxide vapor is produced by vaporizing a liquid mixture of hydrogen peroxide and water which is from 5-95% hydrogen peroxide, more preferably, 25-50% hydrogen peroxide, most preferably, 30-37% hydrogen peroxide. The vapor is introduced to the recirculating airflow and is carried into and through the chamber. The prion deactivation step then takes place over time. The recirculation flow rate, hydrogen peroxide pressure, and temperature are measured and controlled to maintain steady state conditions. Preferably, the concentration of hydrogen peroxide is maintained at below the condensation point of both the hydrogen peroxide and the water vapor to prevent condensation on the surfaces of the items and chamber walls. One embodiment includes increasing the concentration of vapor to above the condensation point, allowing concentrated hydrogen peroxide to condense on contaminated surfaces, and then reforming the vapor during an aeration step by passing dry air over the surfaces.

The concentration of hydrogen peroxide which can be maintained without condensation increases exponentially with temperature. For example, at 20° C., about 1-2 mg/L can be maintained. At 30° C., 2-3 mg/L, at 40° C., 4-5 mg/L, and at 50° C., 8-9 mg/L can be maintained. However, at temperatures above about 60° C., hydrogen peroxide degradation tends to occur more rapidly and prions tend to agglomerate into tighter, harder to attack structures. Accordingly, a temperature of about 45-60° C. is preferred, more preferably 53-57° C., although lower temperatures are effective when exposure times are significantly increased.

Figure 6:
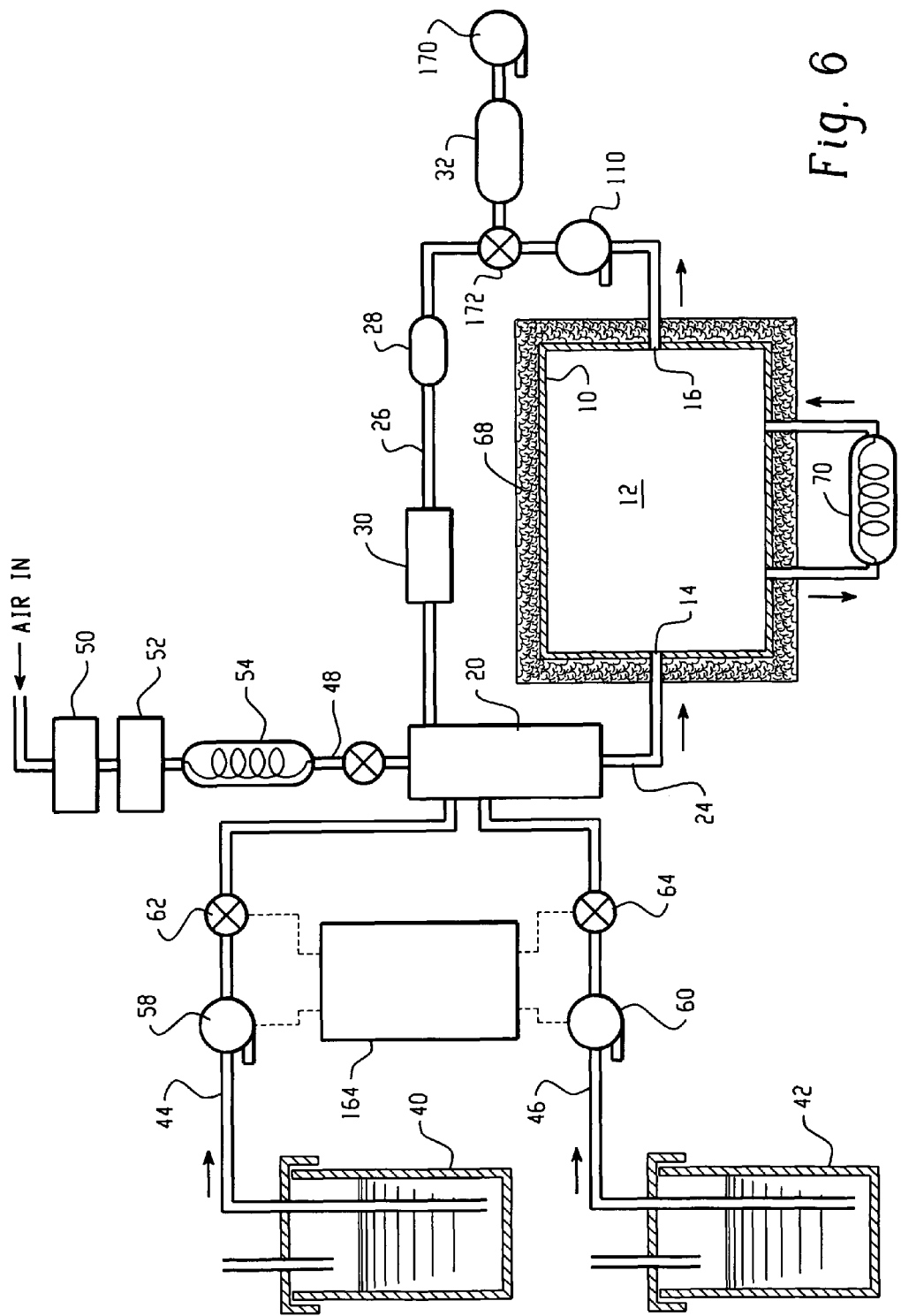
FIG. 6 is a diagrammatic illustration of a prion deactivation system.

With reference to FIG. 6, a suitable prion deactivation vessel includes a chamber wall 10, which defines an interior chamber 12 capable of being pressurized or evacuated. A vapor entry port 14 and an exit port 16 are defined in the chamber wall. A generator 20, supplies the chamber 12 with a sterilant vapor, preferably a vaporized peroxy compound such as hydrogen peroxide, peracetic acid vapor, or mixture thereof, entrained in a carrier gas, such as air.

A circulating system includes a vapor inlet line 24, which carries the vapor from the generator 20 to the entry port 14. The hydrogen peroxide passes through the chamber 12 and leaves the chamber through the exit port 16. Optionally, a return line 26 returns the partially spent hydrogen peroxide vapor to the generator to be refreshed or, as shown in FIG. 6, passes it through a destroyer 28 and a dryer 30. The destroyer converts peroxide to water to be removed in the dryer 30.

In an alternative embodiment, the hydrogen peroxide vapor is recirculated through the chamber for a period of time via a return line without refreshing the vapor with fresh hydrogen peroxide from the generator.

Figure 8:
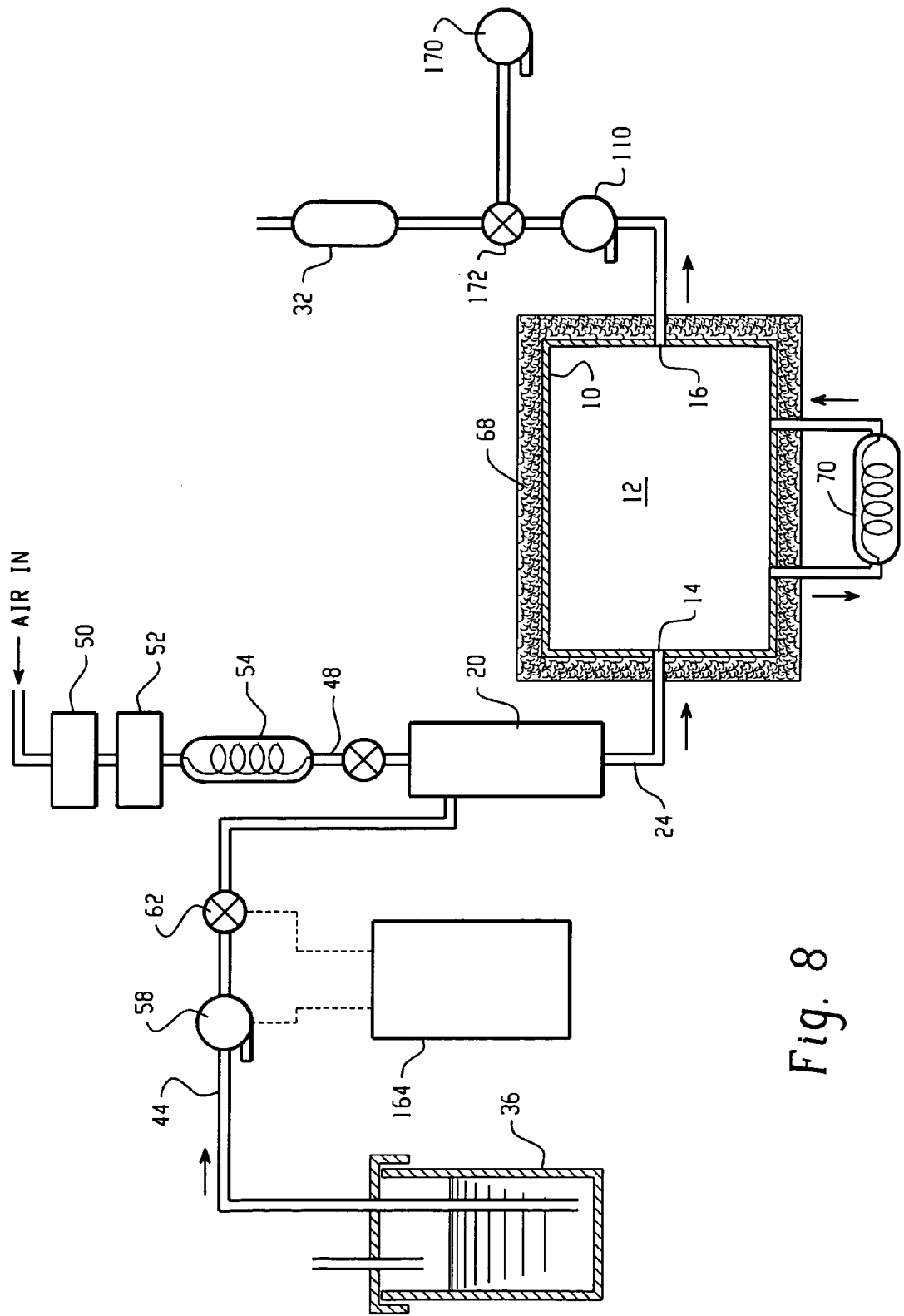
FIG. 8 is a diagrammatic illustration of an alternative embodiment of a prion deactivation system.

Alternatively, as shown in FIG. 8, the vapor leaving the chamber 12 is directed through a catalytic converter 32 which converts the vapor to non-harmful products, such as water and oxygen. As yet another alternative, the vapor leaving the chamber is vented to the atmosphere where sunlight rapidly converts the vapor to water vapor and oxygen. Vaporized hydrogen peroxide is flowed through the chamber 12 until selected sterilization conditions are reached in terms of temperature, pressure, exposure time, and hydrogen peroxide concentration.

Alternatively, an atmospheric system allows input of vapor into an enclosure, holding it in the enclosure for a certain time, and evacuating or aerating the enclosure.

The generator 20 is preferably one which generates a controllable stream of vaporized hydrogen peroxide. A particularly preferred generator is one which vaporizes droplets of liquid hydrogen peroxide by contact with a heated surface and entrains the vapor in a stream of carrier gas, such as air. The gas is then transported with the vapor to the chamber 12.

Alternatively, hydrogen peroxide is generated in situ in the chamber, for example, by treating a compound which releases hydrogen peroxide, such as on heating. Or, other vaporization methods may be employed, such as introducing liquid hydrogen peroxide into an evacuated chamber where it is vaporized by the vacuum.

The liquid hydrogen peroxide is optionally supplied to the generator from a single source 36 as a mixture of hydrogen peroxide in water for example, a 5-95% by weight hydrogen peroxide solution, more preferably, 30-37% hydrogen peroxide (FIG. 8). The liquid components are entirely converted to vapor, so the resulting vapor has the same relative concentration of hydrogen peroxide as the liquid from which it is generated. In a more preferred embodiment, shown in FIG. 6, the components of the vapor are separately contained or contained in higher and lower concentrations so that the composition of the vapor is adjustable by varying the rate of supply of each component to the vaporizer. In the vaporizer, the liquid hydrogen peroxide solution is dripped or sprayed through a nozzle onto a heated surface (not shown), which vaporizes the oxidant without breaking it down. Other vaporizing techniques, such as ultrasonic vaporizers, atomizers, and the like, are also contemplated. A source, such as a reservoir 40 of more concentrated hydrogen peroxide and a source 42 of less concentrated hydrogen peroxide or water are connected with the vaporizer 20 by supply lines 44 and 46, respectively, so that the concentration of hydrogen peroxide in the liquid entering the vaporizer is adjustable.

When a two source system is used, as shown in FIG. 6, destroying and removing the spent vapor in the return line 26 may not be necessary, other than to accommodate pressure changes due to the additional vapor entering through the inlet (or may take place at a lower rate than in a single source system). This is because the relative concentration of the vapor can be adjusted or maintained at a selected level primarily by adjusting the ratio of the two components in the feed. Thus, the overall consumption of hydrogen peroxide liquid is generally lower when separate sources of hydrogen peroxide and water are employed and combined, as required, to achieve a desired hydrogen peroxide concentration in the feed to the vaporizer.

The mixture of water and hydrogen peroxide vapor is mixed with a carrier gas, such as air. The carrier gas is supplied to the vaporizer through a line 48. A filter, such as a HEPA filter 50, preferably filters the incoming air. The air is preferably passed through a drier 52, to remove moisture, and through a heater 54, to raise the temperature of the carrier gas, prior to mixing the carrier gas with the hydrogen peroxide vapor.

First and second pumps 58, 60 pump the hydrogen peroxide and water from the reservoirs 40 and 42. Separately adjustable regulator valves 62, 64 regulate the fluid flow rate through the lines 44, 46. Alternatively, regulation of the flow rates is adjusted by adjusting the pumping rate of the pumps 58, 60. In an alternative embodiment, a single pump replaces the two pumps 58, 60.

A thermal jacket 68, such as a water jacket or a resistance heater, optionally surrounds substantially all of the chamber 12. The jacket 68 serves to maintain a selected temperature within the chamber. A heater 70,1 connected to the thermal jacket 68 heats the jacket. Alternatively, or additionally, the chamber 12 is insulated to reduce heat loss from the chamber 12. In a particularly preferred embodiment, additional insulation of unjacketed areas, such as doors, further serves to maintain the internal temperature of the chamber 12. Items to be deactivated are introduced to the chamber through a door (not shown).

To test the efficacy of hydrogen peroxide against prions, a biological indicator evaluator resistomer (BIER) vessel is optionally used. The BIER vessel operates in a similar manner to the prion deactivation chamber described above, but allows a high level of control and monitoring of the chamber conditions to ensure reproducible results. Additionally, items to be tested are preferably introduced to the chamber through a port once conditions within the chamber have attained the selected conditions for the deactivation study, whereas in a normal prion deactivation system, items to be decontaminated are introduced through a conventional door prior to dehumidification and conditioning of the chamber. In one embodiment, the BIER vessel is simply a standard vapor sterilization vessel which has been adapted for controlled investigation.

Figure 7:
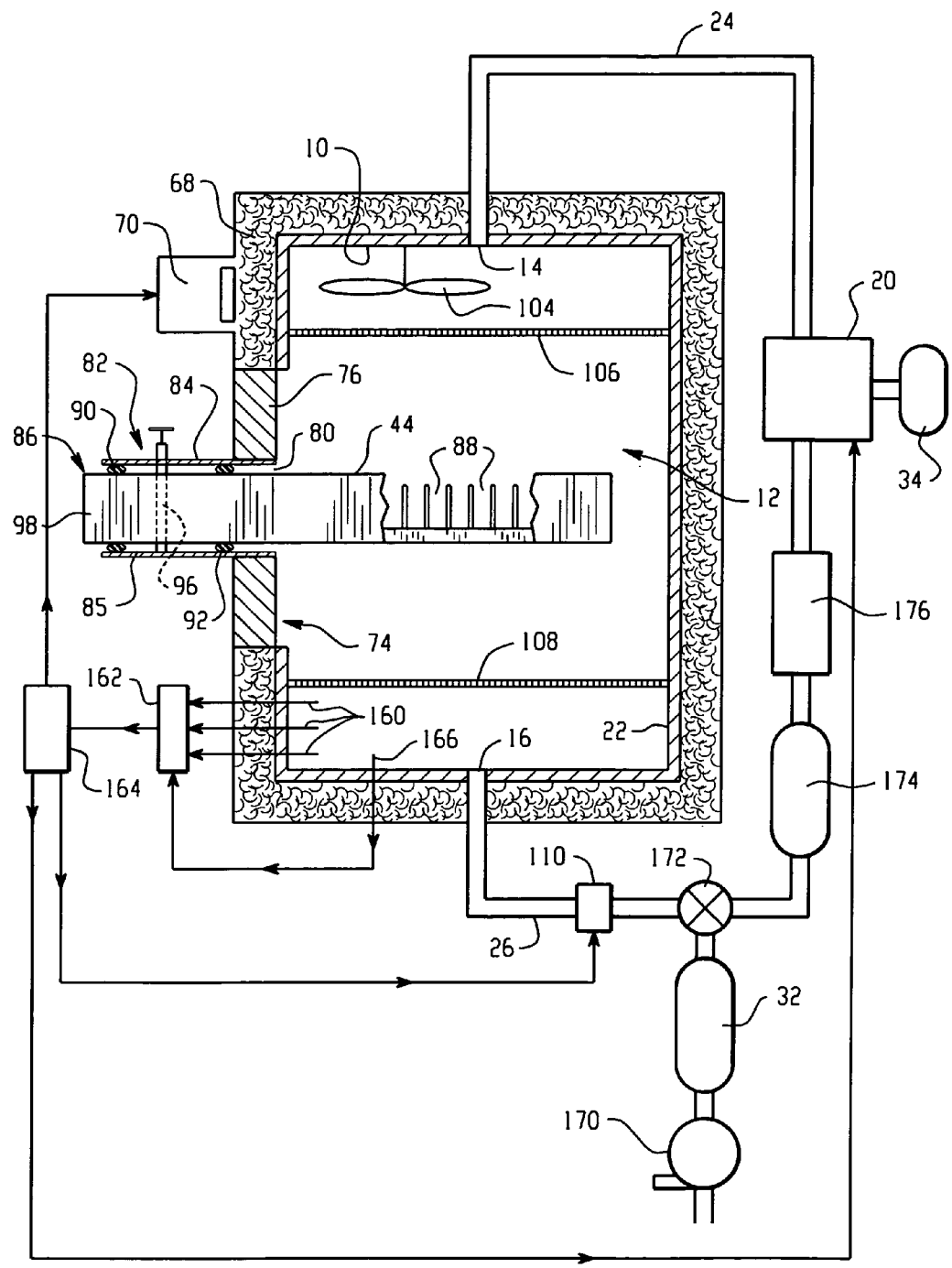
FIG. 7 shows the prion deactivation system of FIG. 6 adapted for control and evaluation of deactivation conditions.

Preferably, as shown in FIG. 7, the test coupons are introduced to the chamber through a small opening 80 formed in the door, or elsewhere in the chamber wall. An access port 82 permits rapid insertion of items to be tested into the chamber without unduly perturbing the chamber conditions. The access port preferably includes a hollow tube 84, which extends outwardly from the door around the opening 80. The tube 84 defines an interior passageway 85, which is shaped to receive a sample holder or D-tube 86. The sample holder 86 has a number of slots 88 or other receptacles for holding items, such as coupons contaminated with prion infected material or biological indicators, to be exposed to the chamber conditions.

Preferably, the access port 82 is constructed to minimize the flow of gas or vapor into or out of the chamber 12 while the coupons and/or biological indicators are being admitted to the chamber 12 to avoid perturbing the equilibrium conditions. The contaminated coupons or biological indicators are thus exposed relatively instantaneously to the preselected equilibrium sterilization conditions. In this respect, two seals 90, 92 are mounted within the tube 84, which form a seal between the sample holder and the tube during insertion and removal. When not in use, the tube interior passageway 85 is closed by a valve 96.

After a selected exposure period, the test coupons and/or indicators are removed from the chamber 12, and evaluated for remaining prion activity and/or microbial activity.

In the illustrated embodiment, a fan, or fans, 104, preferably disposed within the chamber 12, mix the gases within the chamber, thereby improving the uniformity of the mixture and increasing the rate of flow of sterilant over the biological indicators. Perforated upper and lower plates 106 and 108, respectively, are optionally disposed within the chamber 12 to induce a laminar flow of gas through the chamber 12.

Optionally, the flow of vaporized hydrogen peroxide from the generator is further controlled by a flow control device 110, such as a pump, vacuum source or blower, damper, or other regulator, which serves to regulate the flow of vaporized hydrogen peroxide into or out of the chamber. Preferably, the flow control 110 is located in inlet line 24 or return line 26.

Probes 160, such as temperature, pressure and humidity probes, disposed within the chamber 12, serve to measure the chamber environment. The probes are connected to a monitor 162, which monitors the changes in environmental conditions. Preferably, the monitor 162 signals a controller 164 which controls the environmental conditions within the chamber 12 by controlling the heater 70 for regulating the temperature of the thermal jacket 68 and also the operation of the flow control 110, the vaporized hydrogen peroxide generator 20, the pumps 58, 60, and the valves 62, 64.

A sensor 166 is also positioned within the chamber to detect hydrogen peroxide concentration directly and/or detect the concentration of other components of the vapor from which the hydrogen peroxide concentration can be established indirectly.

For vacuum environment testing, a vacuum source, such as a pump 170, evacuates the chamber before, during, or after the sterilization process. Optionally, a three way valve 172 in line 26 is connected to the vacuum pump 170. By switching the valve 172 between a first position, in which chamber gases passing through line 26 are returned to the generator, to a second position in which the chamber gases are directed to the pump 170, the chamber 12 is evacuated. Optionally, a catalytic converter 174 and a drier 176 decompose the peroxy vapor and dry and heat the air before it is reintroduced into the generator 20.

More preferably, the BIER vessel system is used without recirculation of hydrogen peroxide or carrier gas. The mixture of air and hydrogen peroxide flows through the chamber 12 in a single pass then is vented from the chamber via the catalytic converter 174. This provides for better control of the system.

The controller 164 controls one or more of the chamber temperature, chamber pressure, vaporization rate, hydrogen peroxide concentration in the liquid to be vaporized, or vapor flow rate through the chamber in response to measured conditions to maintain the desired prion deactivation conditions within the chamber during an exposure cycle.

It is contemplated that features of the BIER vessel described above are incorporated into the prion deactivation system of FIG. 6, such as the control system, probes, sensors, fans, and the like, for more careful monitoring and control of chamber conditions.

Exposures of coupons contaminated with a prion model, specifically an ileal fluid dependent organism (IFDO), to vapor hydrogen peroxide were carried out in the BIER vessel using different test conditions and exposure times.

Figure 9:
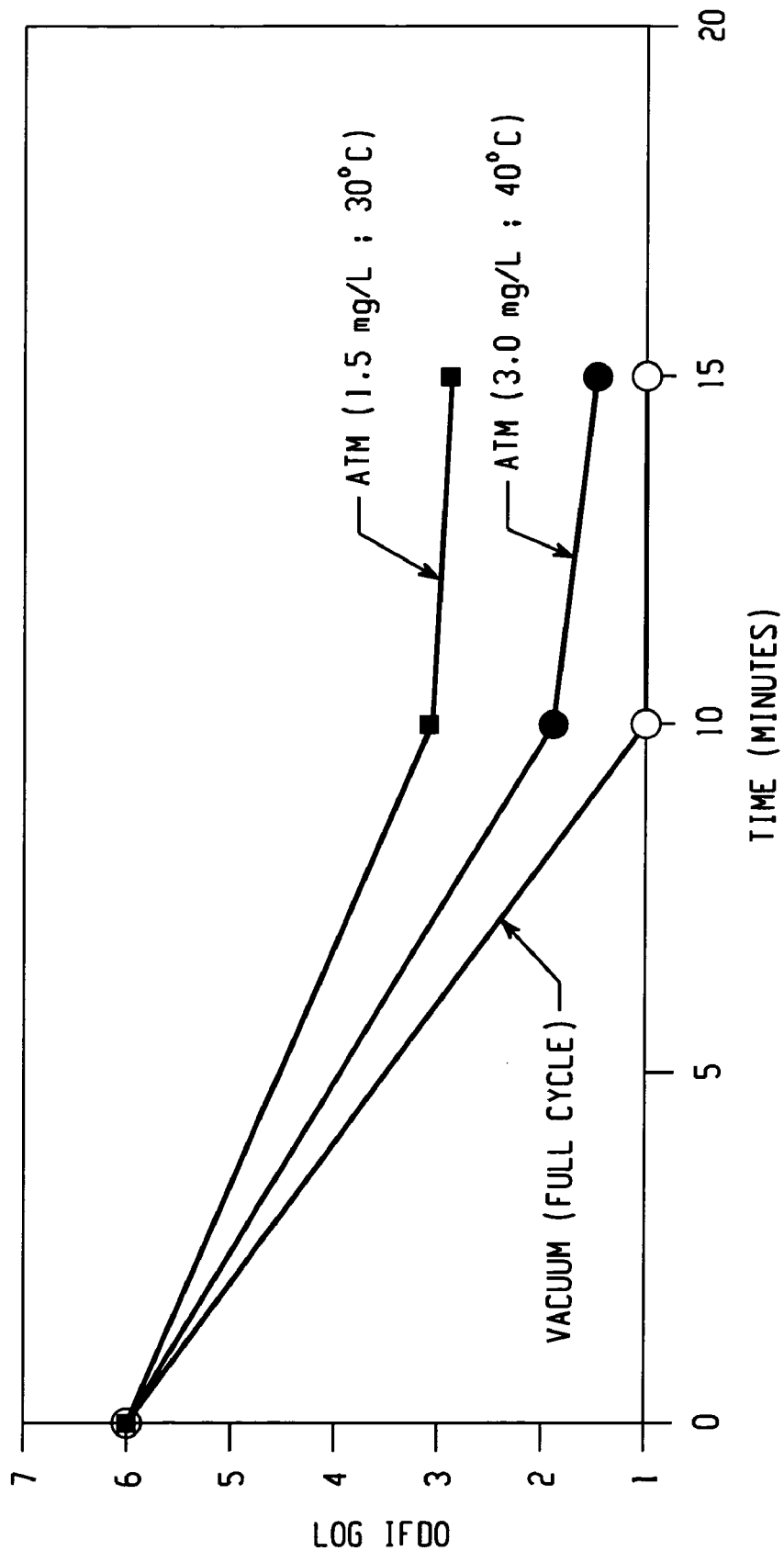
FIG. 9 is a plot of log IFDO versus time for three prion deactivation cycles (ATM=atmospheric conditions)

The results showed that a cycle involving vacuum pulses of hydrogen peroxide, similar to those illustrated in FIG. 5, was more effective at deactivating the prion model (IFDO) than atmospheric conditions (FIG. 9).

When combined with a precleaning step with an alkaline cleaner, as described above, an effective process for ensuring removal and deactivation of any remaining prions on medical instruments or the like is provided.

The instruments or other partially, grossly cleaned items are advantageously transported to the chamber of the prion decontamination system without aeration and drying. Any moisture present on the instruments is removed during the preconditioning/dehumidification phases. Optionally, the instruments are wrapped in a sterile wrap, such as gauze or Tyvek™ wrap, prior to subjecting the instruments to hydrogen peroxide decontamination. A number of alternative cleaning and decontaminating procedures are also contemplated. For example, a combined cleaning and sterilization system may be used. Or, items may be placed in an enclosed tray for sterilization and/or cleaning. Such a tray may be sealed after the decontamination process is complete to maintain the sterility of the items until reuse.

A prion deactivation process involving an alkaline cleaning step followed by a hydrogen peroxide or other vapor sterilant step is not only effective for removing/and or deactivating prions but also is effective for sterilization of the items. Thus, medical instruments and other devices need not be subjected to a separate sterilization process to ensure that microorganisms which may pose hazards to patients or those handling the instruments are also destroyed.

Accordingly, a combination of an alkaline cleaning product wash at an alkali concentration of about 0.02M to about 0.2M followed by a vapor hydrogen peroxide treatment is an effective alternative to a conventional treatment (1N NaOH and/or heating to 120° C. for one hour followed by microbial decontamination) and is less damaging to the medical instruments or other items being treated.

The process thus described is optionally combined with additional cleaning and/or microbial decontamination or prion deactivation steps. For example, a liquid sterilization/prion deactivation step optionally precedes the gaseous oxidant step. For example, instruments are alkaline cleaned, rinsed, sterilized with a peracetic acid solution, wrapped in a sterile wrap or placed in a tray, then finally sterilized/prion deactivated with hydrogen peroxide.

Figure 10:
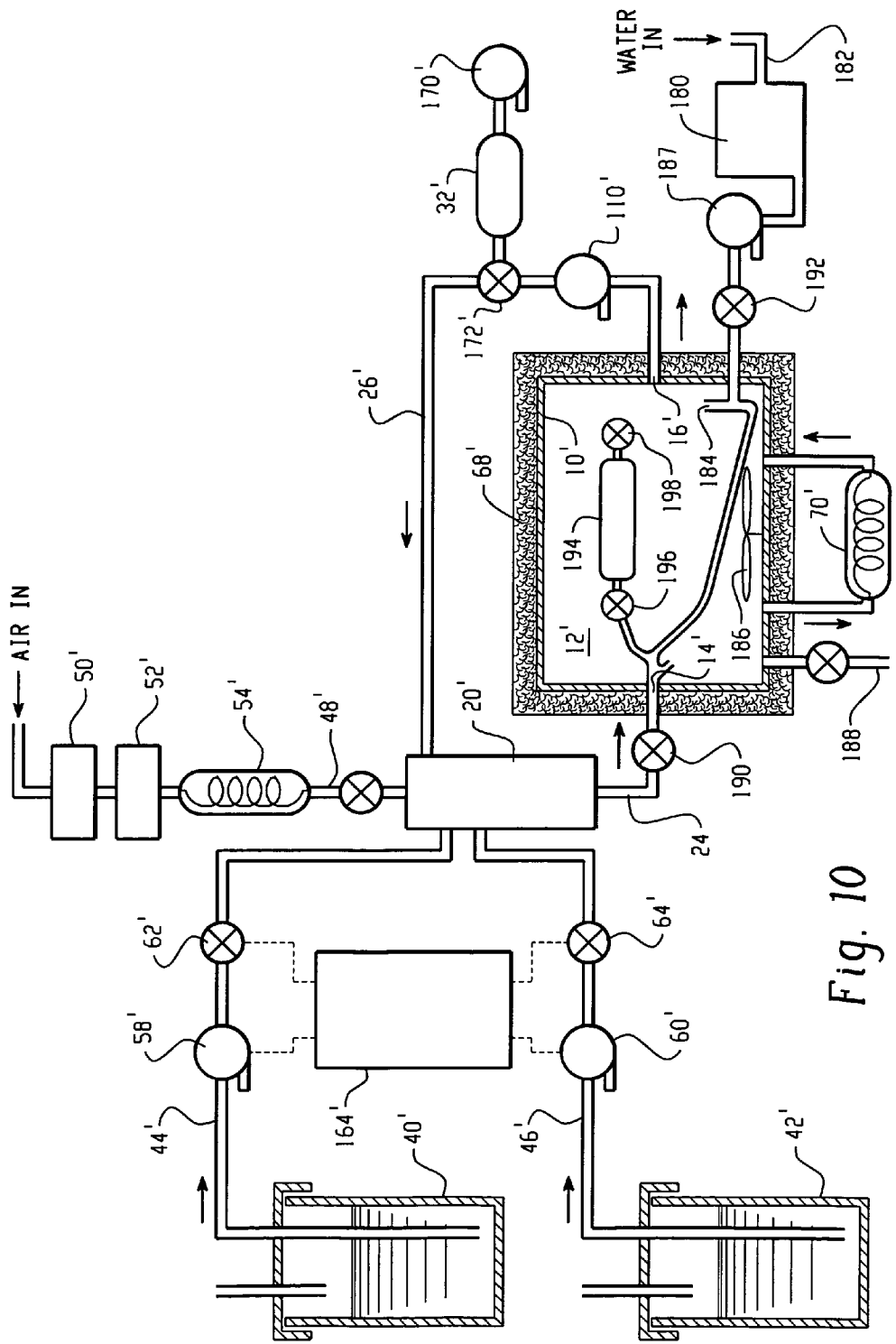
FIG. 10 is a schematic illustration of a combined washer and prion deactivation system.

In one embodiment, shown in FIG. 10, an apparatus which acts as both a washer and a prion decontamination vessel is used. This avoids the need to remove the alkaline-cleaned items and transport them to a separate vapor treatment vessel. The device is similar to that shown in FIG. 6. Like parts are identified with a prime (') with new components given new numbers. Items are loaded into a chamber 10' of the apparatus and washed with an alkaline cleaner and rinsed. In one embodiment, a first cleaning step uses a first cleaner (e.g., alkaline). This is followed by a rinse step, then another cleaning step with a second cleaner (e.g., enzymatic) and a further rinse step.

The concentrated alkaline cleaner is supplied in liquid or solid form to a well 180. Water (preferably heated to about 50-60° C.) is introduced to the well through a flow line 182 and carries the alkaline or other cleaner in solution to nozzles 184 located in the chamber 10'. An agitator 186 agitates the liquid in the chamber. Optionally, a pump 187 supplies the cleaning solution to spray nozzles under pressure. After a period sufficient to remove the bulk of any prion contaminated material from the items, the alkaline cleaner is emptied from the chamber via a drain line 188. Rinse water is introduced to the chamber for one or more rinse cycles and drained. The moisture in the chamber is then reduced by flowing dry air through the chamber from line 48'. Optionally, the chamber is capable of withstanding below atmospheric pressures and is evacuated with a vacuum pump 110'. Hydrogen peroxide vapor from a generator 20' is then introduced to the chamber mixed with the sterile air. In a flow through system, the hydrogen peroxide/carrier gas is flowed through the chamber for a sufficient time to effect prion deactivation. Alternatively, a pulse system similar to that described above in connection with FIG. 5, is used. In this system, the chamber is evacuated and then a pulse or pulses of hydrogen peroxide vapor are introduced.

The chamber is preferably fitted with temperature and pressure probes, chemical sensors, and a control system similar to those previously described in connection with FIG. 7 to allow careful monitoring and control of conditions within the chamber. Valves 190, 192 are provided for selectively closing off the vapor and cleaning liquid supplies, respectively.

Optionally, one or more items to be washed and prion decontaminated are enclosed in a tray 194 connected with vapor and cleaning liquid ports 14' and 184. The cleaning fluid and/or vapor is flowed through the tray. At the end of the cycle, valves 196, 198 are closed to seal access to the tray, thus sealing the tray against airborne contaminant ingress until use.

While the invention has been described with particular reference to prions, it will be appreciated that other proteinaceous materials may also be deactivated by the process herein described. Further, while prion deactivation has been described with particular reference to a decontamination vessel or chamber, it is also contemplated that rooms or other enclosures and their contents, such as aseptic filling lines, are cleaned and prion deactivated in a manner similar to that described above.

Without intending to limit the scope of the invention, the following examples show the effects of vapor sterilization on prion models.

EXAMPLES

Example 1

To test the efficacy of vapor hydrogen peroxide a BIER vessel as described above (FIG. 7) is used to study the reduction in a prion model (IFDO). Stainless steel coupons are inoculated with samples of a suspension of IFDO in a sterile medium and dried. The dried coupons are exposed to one of three processes. In the first process, coupons are exposed to vapor hydrogen peroxide at atmospheric pressure and at a concentration of 1.5 mg/l and a temperature of 30° C. for 15 minutes. In the second process, inoculated coupons are exposed to vapor hydrogen peroxide at atmospheric pressure and at a concentration of 3 mg/l and a temperature of 40° C. for 15 minutes. In the third process, a vacuum pump is applied to the chamber to reduce the pressure to less than about 10 Torr ($1.33 \times 10^3$ Pa). Six pulses of hydrogen peroxide vapor at 30° C. are then introduced at a concentration of about 2.5 mg/ml, each spaced by an approximately 10 Torr evacuation step, as described in connection with FIG. 5. FIG. 9 shows the results obtained. Note that for the vacuum cycle tests, the coupons are exposed to the full cycle, and thus are independent of the time shown in the graph.

The amount of IFDO remaining is obtained by culturing the IFDO remaining on the coupons and observing the growth of colonies, if any. The number of colonies developed on the vacuum treated samples is less than 1 log, i.e., at least a six log reduction in IFDO in the vacuum process.

Example 2

The effects of temperature and concentration of vapor hydrogen peroxide are investigated in a vacuum sterilizer having a coupon introduction port similar to that shown in FIG. 7. Stainless steel coupons are inoculated with samples of a suspension of IFDO in a sterile medium and dried. The dried coupons are exposed in the BIER vessel, which is first lowered to a pressure of less than about 10 Torr ($1.33 \times 10^3$ Pa). A single pulse of hydrogen peroxide vapor at a selected temperature and concentration is introduced. The results are shown in Table 4.

TABLE 4

| Experiment | Temperature | Hydrogen peroxide Concentration | Log reduction in IFDO organisms |
| --- | --- | --- | --- |
| 1 | 30° C. | 2.2 mg/l | 3-4 |
| 2 | 40° C. | 5.5 mg/l | 8 |
| 3 | 40° C. | 2.0 mg/l | 5.5 |
| 4 | 50° C. | 7.5 mg/l | 8 |

The amount of IFDO remaining is obtained by culturing the IFDO remaining on the coupons and observing the growth of colonies, if any. The number of colonies developed from IFDO remaining on the vacuum treated samples is less than 1 log, i.e., at least a six log reduction in IFDO in the vacuum process.

Example 3

Experiments designed to evaluate the breakdown of proteins are carried out using BSA protein as a model for prions. Aliquots of a suspension of BSA are droppered onto stainless steel coupons and dried. The protein contaminated coupons are examined before or after a vapor hydrogen peroxide treatment process (1 hour in a STERIS VHP 1000™ sterilizer using about 1.5 mg/L vapor hydrogen peroxide at 25° C.). The recovered protein is evaluated by gel electrophoresis to separate out complete proteins from smaller fragments. The results show that VHP effectively destroys proteins.

Example 4

Figure 11:
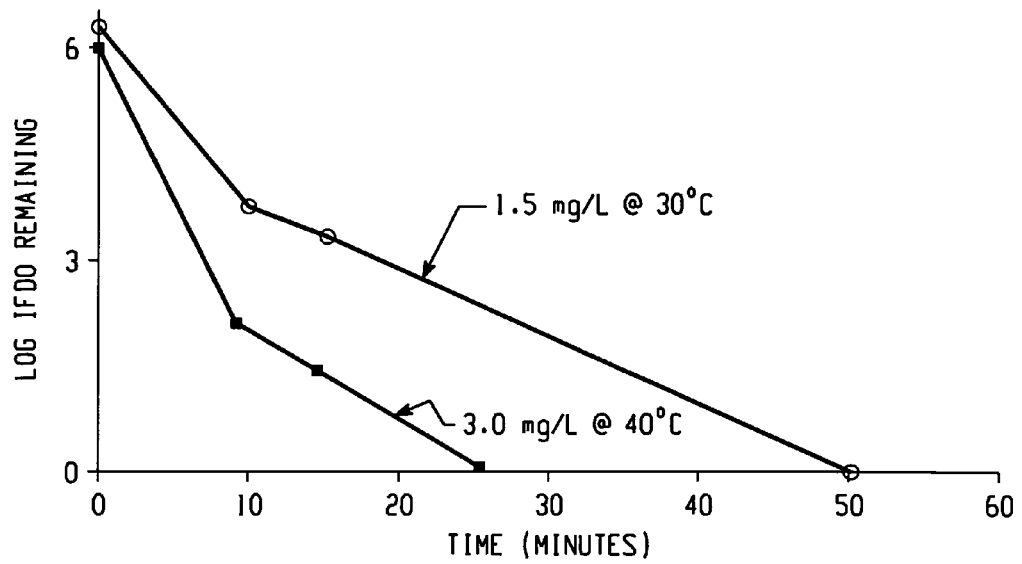
FIG. 11 is a plot of IFDO concentration versus time for IFDO inoculated coupons exposed to hydrogen peroxide vapor at 1.5 mg/L and 30° C. and at 3.0 mg/L and 40° C.

The effect of temperature and concentration on IFDO protein is evaluated under atmospheric conditions. Coupons are prepared by dropping aliquots of a suspension of IFDO in water onto stainless steel coupons which are then dried. The coupons are placed into pouches formed from Tyvek™ wrap. The wrapped coupons are exposed to hydrogen peroxide at 1.5 mg/L and 30° C. or 3.0 mg/L and 40° C. FIG. 11 shows the concentration of IFDO remaining on the coupons over time. The effects of higher temperatures and concentrations are significant.

Example 5

Figure 12:
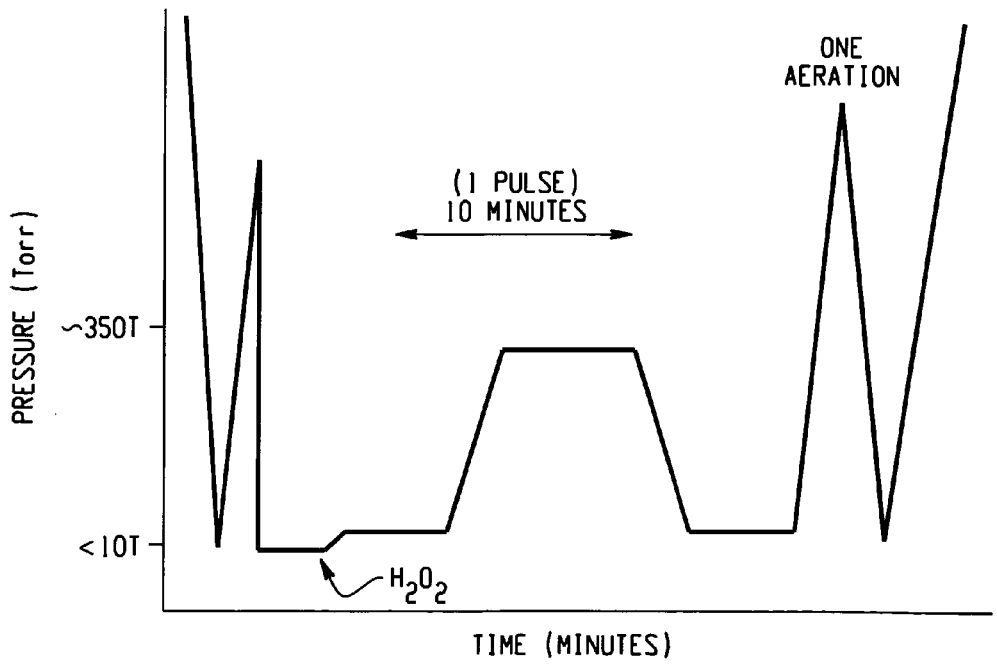
FIG. 12 is a schematic illustration of an exemplary vacuum/vapor hydrogen peroxide cycle.

IFDO inoculated coupons are prepared as for Example 4 and exposed in a vacuum chamber to a vapor hydrogen peroxide vacuum cycle, as illustrated schematically in FIG. 12. After two evacuation steps, a pulse (or in one case, two pulses) of hydrogen peroxide is introduced to the chamber for 10 minutes. The chamber is then evacuated and followed by an aeration pulse. After further evacuation, the chamber is brought up to ambient pressure and the coupons removed. Table 5 shows the results for different temperatures and vapor hydrogen peroxide concentrations in terms of the log reduction in IFDO species.

TABLE 5

| Temperature (° C.) | Vapor Hydrogen Peroxide Conc. (mg/L) | No. of Pulses | Log Reduction (IFDO) |
| --- | --- | --- | --- |
| 30° C. | 2.2 | 1 | 3-4 |
| 40° C. | 5.5 | 1 | >6 |
| 40° C. | 2.2 | 1 | 3-4 |
| 40° C. | 2.2 | 2 | >6 |
| 50° C. | 7.5 | 1 | >6 |

Example 6

Samples are prepared similar to those for Example 4, but in this case are further contaminated with 0, 10, or 50%. blood. The samples are exposed to vapor hydrogen peroxide sterilization cycles as shown in FIG. 12, with either three or six pulses of hydrogen peroxide vapor at 30° C. or 50° C. The results shown in Table 6 indicate the importance of cleaning items prior to a prion decontamination step.

TABLE 6

| Temperature (° C.) | Vapor Hydrogen Peroxide Conc. (mg/L) | No. of Pulses | Soil | Log Reduction (IFDO) |
| --- | --- | --- | --- | --- |
| 30 | 2.0 | 6 | None | >7 |
| 30 | 2.0 | 6 | 10% blood | 4-5 |
| 30 | 2.0 | 6 | 50% blood | 1-2 |
| 50 | 7.0 | 3 | None | >7 |
| 50 | 7.0 | 3 | 10% blood | >7 |
| 50 | 7.0 | 3 | 50% blood | 3-4 |

By first removing all (represented by 0% blood) or most (represented by 10% blood) of the soil, it can be seen that a vapor hydrogen peroxide cycle can be effective at removal of prions, particularly when a 50° C. cycle and a 7.0 mg/L hydrogen peroxide concentration are employed.

Example 7

Coupons are prepared by dropping aliquots of a suspension of human CJD-contaminated brain homogenate in water onto stainless steel coupons which are then dried. The coupons are placed into pouches formed from Tyvek™ wrap. The wrapped coupons are exposed to various treatment processes, without a precleaning step, either at atmospheric pressure or under vacuum conditions, both with and without hydrogen peroxide. After exposure, the coupons are extracted in phosphate buffer saline by sonification. The extracts are concentrated, separated by SDS-PAGE, and Western blotted. The presence or absence of prion protein ($P_R P^{SC}$) is determined using an antibody array. The results shown in Table 7 indicate that vapor hydrogen peroxide is effective at destruction of the harmful form of the prion protein.

TABLE 7

| Temperature (° C.) | Vapor Hydrogen Peroxide Conc. (mg/L) | Conditions | $P_R P^{SC}$ Detected |
|---|---|---|---|
| 25 | 1.7 | 3 hours exposure, atmospheric pressure | No |
| 25 | 0 | 3 hours exposure, atmospheric pressure | Yes |
| 30 | 2.2 | Vacuum conditions, six pulses of vapor | No |
| 50 | 7.0 | Vacuum conditions, three pulses of vapor | No |
| 50 | 0 | Vacuum conditions | Yes |

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of deactivating prions which is less damaging to surfaces than a conventional treatment with at least one of 1N sodium hydroxide and heating to 120° C. for one hour followed by microbial decontamination, comprising:
   pretreating surfaces that carry prion infected material with an alkaline cleaner, whereby at least a portion of the prions remaining in a residual film on the surfaces are destroyed and thereafter, optionally rinsing and drying the surfaces; and
   treating the surfaces with the residual film thereon with an oxidizing agent in gaseous form to deactivate residual prions in the film.

2. The prion deactivation method of claim 1, wherein the oxidizing agent includes hydrogen peroxide vapor.

3. The prion deactivation method as set forth in claim 1, wherein the alkaline cleaner includes a strong alkali of the group consisting of alkali metal hydroxides, alkali earth metal hydroxides, and combinations thereof.

4. The prion deactivation method as set forth in claim 3, wherein the strong alkali includes one or more of sodium hydroxide and potassium hydroxide.

5. The prion deactivation method as set forth in claim 1, wherein the alkaline cleaner further includes an additive selected from the group consisting of surfactants, cationic polymers, anti-redeposition agents, corrosion inhibitors, buffers, chelating agents, and combinations thereof.

6. The prion deactivation method as set forth in claim 5, wherein the step of treating the surfaces with an oxidizing agent in gaseous form is carried out at 45-60° C.

7. The prion deactivation method as set forth in claim 6, wherein the cleaning and gaseous oxidizing agent treatment steps are carried out in a temperature range between 50° C. and 60° C.

8. The prion deactivation method as set forth in claim 1, further including:
   rinsing the alkaline cleaner from the surfaces prior to the gaseous oxidizing agent treatment step.

9. The prion deactivation method as set forth in claim 8, further including:
   after rinsing the surface, wrapping the surface in a microbe barrier; and
   subjecting the wrapped surface to the gaseous oxidizing agent treatment step.

10. The prion deactivation method as set forth in claim 1, wherein the cleaning and gaseous oxidizing agent treatment steps are carried out in the same vessel.

11. The prion deactivation method as set forth in claim 10, wherein the cleaning and gaseous oxidizing agent treatment steps are carried out without intermediate removal of the surfaces from the vessel.

12. The prion deactivation method as set forth in claim 1, wherein the gaseous oxidizing agent treatment step includes:
   a) introducing the surface to be treated to a chamber;
   b) reducing the pressure within the chamber to below atmospheric pressure; and
   c) introducing hydrogen peroxide vapor to the chamber.

13. The prion deactivation method as set forth in claim 12, wherein the gaseous oxidizing agent treatment step includes repeating steps b) and c) one or more times.

14. The prion deactivation method as set forth in claim 12, wherein step b) includes reducing the pressure within the chamber to about 10 Torr or below.

15. The method as set forth in claim 12, further including:
   after step c), reducing the pressure within the chamber to below atmospheric pressure; and
   raising the pressure to a higher subatmospheric pressure with filtered air.

16. A prion deactivation method comprising:
   pretreating surfaces that carry prion infected material with an alkaline cleaner that deactivates prions; and
   treating the surfaces with an oxidizing agent in gaseous form to deactivate any remaining prions, the oxidizing agent including hydrogen peroxide vapor, the oxidizing agent treating step being carried out at from about 45-60° C.

17. The prion deactivation method as set forth in claim 16, wherein the step of treating the surfaces with an oxidizing agent in gaseous form follows the step of pretreating the surfaces with an alkaline cleaner, the surface being a surface of a medical instrument which is susceptible to damage by strong alkali treatment.

18. A prion deactivation system for removing and deactivating prions on an item comprising:
- a chamber for receiving the item;
- a well fluidly connected with the chamber for receiving a concentrated alkaline cleaner;
- a supply of water fluidly connected with the well for providing water to mix with the concentrated alkaline cleaner and form an alkaline cleaning solution;
- a source of hydrogen peroxide vapor fluidly connected with the chamber.

19. The prion deactivation system as set forth in claim 18, further including:
- a heater for heating the chamber to a temperature of at least 30° C.

20. A method of deactivating prions comprising:
- pretreating surfaces that carry prion infected material with a cleaner that removes prions, the cleaner having an alkali concentration of about 0.02M to about 0.2M and comprising a surfactant; and
- deactivating prions on the surfaces with an oxidizing agent in gaseous form, the oxidizing agent including hydrogen peroxide.

21. The method of claim 20, wherein the oxidizing agent is at a temperature of from 45-60° C.

22. A method of deactivating prions on surfaces of medical devices which are incompatible with treatments which include strong alkali or treatments which include soaking the instrument in concentrated hydroxide or hypochlorite for two hours followed by one hour in an autoclave, the method comprising:
- pretreating surfaces that carry prion infected material with a cleaner that removes prions, the cleaner including a surfactant and having an alkali concentration of about 0.02M to about 0.2M; and
- at a temperature of 25° C.-60° C., treating the pretreated surfaces with an oxidizing agent in gaseous form which deactivates prions remaining on the surfaces.

* * * * *